United States Patent [19]

Sherif et al.

[11] Patent Number: 4,496,527

[45] Date of Patent: * Jan. 29, 1985

[54] DICALCIUM PHOSPHATE DIHYDRATE HAVING IMPROVED MONOFLUOROPHOSPHATE COMPATIBILITY AND PROCESS FOR THE PREPARATION THEREOF

[75] Inventors: Fawzy G. Sherif, Stony Point; Helmut W. Majewski, Nyack; Francis A. Via, Yorktown Heights, all of N.Y.

[73] Assignee: Stauffer Chemical Company, Westport, Conn.

[*] Notice: The portion of the term of this patent subsequent to Dec. 11, 2001 has been disclaimed.

[21] Appl. No.: 511,973

[22] Filed: Jul. 8, 1983

Related U.S. Application Data

[63] Continuation of Ser. No. 336,214, Dec. 31, 1981, abandoned.

[51] Int. Cl.³ ............................................. C01B 25/32
[52] U.S. Cl. ...................................... 423/309; 423/308
[58] Field of Search ....................... 423/308, 309, 311

[56] References Cited

U.S. PATENT DOCUMENTS

| | | | |
|---|---|---|---|
| 2,036,760 | 4/1936 | Knox | 423/309 |
| 3,012,852 | 12/1961 | Nelson | 423/309 |
| 3,294,486 | 12/1966 | Cremer et al. | 423/309 |
| 4,312,843 | 1/1982 | Monty et al. | 423/267 |

*Primary Examiner*—John Doll
*Assistant Examiner*—Wayne A. Langel
*Attorney, Agent, or Firm*—Hensley M. Flash

[57] ABSTRACT

Dicalcium phosphate dihydrate compositions having improved monofluorophosphate compatibility are prepared by adding pyrophosphoric acid to the dicalcium phosphate dihydrate reactor and terminating the reaction by which the dicalcium phosphate dihydrate is formed at a pH ranging from above about 2.2 to below about 4.9.

4 Claims, No Drawings

DICALCIUM PHOSPHATE DIHYDRATE HAVING IMPROVED MONOFLUOROPHOSPHATE COMPATIBILITY AND PROCESS FOR THE PREPARATION THEREOF

This is a continuation of application Ser. No. 336,214 filed Dec. 31, 1981, abandoned.

BACKGROUND OF THE INVENTION

The present invention relates to dicalcium phosphate compositions having improved monofluorophosphate compatibility, and to a process for the preparation thereof.

Dicalcium phosphate dihydrate has been used as a dental polishing agent in toothpastes and powders for many years.

This material is typically produced by first reacting a slaked lime slurry with phosphoric acid to form a dicalcium phosphate dihydrate precipitate, and then separating the dicalcium phosphate dihydrate precipitate from the mother liquor, after which it is dried and milled to form the final product as a fine powder.

One serious problem which was initially encountered in the use of dicalcium phosphate dihydrate in toothpaste was the tendency of the dicalcium phosphate to "set-up" and become lumpy. When this occurs in toothpaste formulations, it makes it difficult to extrude the toothpaste from the tube in which it is usually packaged.

A second problem was encountered with the advent of the use of monofluorophosphate additives in toothpaste formulations. It was found that the monofluorophosphate components would react with the dicalcium phosphate whereby the monofluorophosphate component was converted from a water-soluble form to an insoluble form. Since the beneficial effect of monofluorophosphate additives in toothpaste are understood to be derived principally from the water-soluble form, it has become important to develop toothpaste formulations which permit an effective amount of monofluorophosphate component to remain in the water-soluble state.

The term "monofluorophosphate-compatibility" has been used as a term-of-art to describe the tendency of such formulations to permit the monofluorophosphate component to remain in the water-soluble state.

The monofluorophosphate compatibility of a particular formulation may be determined by a variety of methods. Preferably, the monofluorophosphate compatibility of a formulation is determined by actually preparing the formulation, placing it in storage for a predetermined period of time under controlled conditions, and then determining the amount of water-soluble monofluorophosphate which remains in the formulation after having been stored under these conditions. Alternatively, a simulated formulation, such as the dicalcium phosphate dihydrate to be tested, glycerine and a known amount of a monofluorophosphate component, such as sodium monofluorophosphate can be "quick aged" by maintaining it at an elevated temperature for one or more hours, and then determining the amount of water-soluble monofluorophosphate remaining after such conditioning. There are, of course, many other methods for measuring the relative monofluorophosphate compatibility of various samples of dicalcium phosphate dihydrate.

U.S. Pat. No. 2,287,699 teaches that dicalcium phosphate dihydrate may be stabilized by adding a small amount of an alkali metal pyrophosphate to the mother liquor, at a controlled pH, during the preparation of the dicalcium phosphate. Specifically, it is taught that after precipitation of the dicalcium phosphate in the mother liquor, a small amount of alkali metal pyrophosphate should be added and the entire slurry then heated for a short period of time, while maintaining the pH of the mother liquor above 7.

Alternatively, the precipitate may be treated during the subsequent washing step.

It is also known to those skilled in the art that other forms of pyrophosphate can also be used to stabilize the dicalcium phosphate.

Another method for stabilizing dicalcium phosphate is disclosed in U.S. Pat. 2,018,410. This patent teaches that dicalcium phosphate can be stabilized by the addition thereto of a magnesium salt such as trimagnesium phosphate, magnesium sulfate, magnesium stearate, or dimagnesium phosphate.

Copending U.S. patent application Ser. No. 106,637 now U.S. Pat. No. 4,312,843 teaches a method for preparing dicalcium phosphate dihydrate compositions having improved monofluorophosphate compatibility which involves the addition of pyrophosphoric acid to the reaction mixture and termination of the reaction within a very limited pH range of from about 4.9 to about 5.5.

Surprisingly and unexpectedly in view of the teachings of the prior art, it has now been found that improved monofluorophosphate compatibility can be achieved with the addition of pyrophosphoric acid and termination of the reaction at pHs below about 4.9.

SUMMARY OF THE INVENTION

In accordance with the present invention there is now provided a process for preparing dicalcium phosphate dihydrate having improved monofluorophosphate compatibility comprising the steps of
(a) reacting a slaked lime slurry with phosphoric acid to form a monocalcium phosphate solution;
(b) adding to the solution additional slaked lime slurry and pyrophosphoric acid in amounts sufficient to form a dicalcium phosphate dihydrate slurry having a pH ranging from above about 2.2 to below about 4.9; and
(c) separating the dicalcium phosphate dihydrate from the slurry.

DETAILED DESCRIPTION OF THE INVENTION

In accordance with the present invention it has now been discovered that termination of the reaction at pHs ranging from above about 2.2 to below about 4.9 together with addition of pyrophosphoric acid to the reaction mixture results in the formation of dicalcium phosphate dihydrate having improved monofluorophosphate compatibility. This is contrary to the prior art which teaches the pH range of from 4.9 to 5.5.

It has now been found that the formation of dicalcium phosphate dihydrate crystals during addition of the lime slurry to the monocalcium phosphate solution begins at a pH of about 2.2, and that the crystals which are formed at that point have a very high degree of monofluorophosphate compatibility. Yield at this low pH however, is relatively low.

The dicalcium phosphate dihydrate crystals which are formed at pHs between about 2.2 and about 3 appear to have the same very high degree of monofluorophosphate compatibility, but yield increases as additional lime slurry is added to increase the pH. Thus, higher pHs are accompanied by higher yields.

It appears that the crystals which are formed at pH's above about 3.3 are less compatible with monofluorophosphate than those formed at lower pH's but that the overall monofluorophosphate compatibility of the total mixture of crystals formed remains quite high even at a final pH of about 4.9.

The lime which is used in the practice of the present invention is the same type rotary kiln lime or shaft kiln lime as is used in conventional dicalcium phosphate processes.

The slaked lime slurry is prepared by mixing lime with either water or recycled mother liquor (i.e., that which remains after removal of dicalcium phosphate dihydrate product from the final slurry), or both, in amounts from about 100 to about 150 grams CaO/liter and at a temperature preferably ranging from about 70° C. to about 74° C. At higher concentrations the mixture will become a gelatinous mass which will be difficult to handle, while at concentrations below the range specified the process "payload" will be unnecessarily reduced.

The slaked lime slurry is then added to phosphoric acid to form a monocalcium phosphate solution.

The acid which is used is preferably a food grade phosphoric acid, preferably at an initial concentration of about 85%. Varying amounts of recycled mother liquor may also be added to the lime slurry and phosphoric acid, with the specific amount in each case being determined in accordance with the preferences of the individual practitioner. The compositional range of the monocalcium phosphate solution will be approximately as follows:

|  | High (Wt. %) | Low (Wt. %) |
|---|---|---|
| CaO | 4 | 2 |
| $P_2O_5$ | 22 | 12 |
| pH | 2 | 1 |

These ranges are set forth as examples of those which are typical, and are in no way intended to be limitations on the scope of the present invention. Those skilled in the art will understand that higher and lower amounts may also be used, provided that the reaction mixture meets the requirements of the practitioner.

When the lime slurry and phosphoric acid are brought together under the conditions specified above, a reaction will ensue and a monocalcium phosphate solution will be formed. The essential completion of the reaction will be indicated by a steadystate pH of from about 1.0 to about 2.0.

The preparation of the monocalcium phosphate solution can be carried out as a continuous, batch or semi-batch process.

Once the monocalcium phosphate solution has been formed, the pyrophosphoric acid and additional slaked lime slurry are added to form the dicalcium phosphate dihydrate slurry. This reaction is exothermic and external cooling is required to control the reaction temperature. The reaction temperature should preferably be controlled at or below about 50° C.

It is preferable to first add the additional slaked lime slurry to the monocalcium phosphate solution until a desired pH is reached, and then the pyrophosphoric acid is added. The minimum amount of pyrophosphoric acid which should be added is about 0.1% by weight of dicalcium phosphate dihydrate to be prepared while the maximum added should be about 1.0%. The pH will, of course, drop slightly when the pyrophosphoric acid is added.

Although it is preferable to add the pyrophosphoric acid and slaked lime slurry to the monocalcium phosphate solution in the sequence just described, it is within the scope of the invention to add these two ingredients in other than that sequence. It is, however, important that the final pH after both of these ingredients are added, ranges from above about 2.2 to below about 4.9 and preferably, that is be from about 3.3 up to about 4.7.

The amount of pyrophosphoric acid added should range from about 0.1% to about 1.0% by weight of dicalcium phosphate dihydrate to be produced, and preferably, from about 0.3% to about 0.4%.

Once the dicalcium phosphate dihydrate slurry has been formed as described above, the dicalcium phosphate dihydrate product is separated from the mother liquor. The mother liquor may then be recycled to the beginning of the process, or discarded.

The separation of the dicalcium phosphate dihydrate from the slurry can be accomplished by any of several conventional techniques. These techniques include, but are not limited to, decantation, centrifugation, filtration and the like, although decantation is preferred because of its simplicity.

The stabilizers which are usually added to dicalcium phosphate dihydrate are intended to prevent the "caking" and "lumping" which occurs in unstabilized dicalcium phosphate dihydrate as a result of dehydration. There are many stabilizers known to be useful for this purpose. These include, but are not limited to dimagnesium phosphate, trimagnesium phosphate, magnesium stearate and magnesium sulfate. The amount of stabilizer added ranges from about 0.5% to about 5.0% by weight of dicalcium phosphate dihydrate. Preferred stabilizers for use in the practice of the present invention are dimagnesium phosphate trihydrate, trimagnesium phosphate octahydrate, and mixtures thereof.

It is preferred to add the stabilizer to the dicalcium phosphate dihydrate by dry-blending these two components after the dicalcium phosphate dihydrate has been dried or after it has been dried and milled. It is, however, within the scope of the invention to add the stabilizer to the product slurry before separating the dicalcium phosphate dihydrate therefrom; or to the "wet" dicalcium phosphate dihydrate prior to drying and milling.

In order that the present invention be more fully understood, the following examples are given by way of illustration. No specific details or enumerations contained therein should be construed as a limitation on the present invention except insofar as they appear in the appended claims.

EXAMPLE 1

Slaked lime slurry (10.85% CaO) prepared by slaking lime with recycled mother liquor from a dicalcium phosphate dihydrate synthesis, was added with stirring to 750 grams of a clear solution of monocalcium phosphate prepared using the same recycled mother liquor, until the pH reached 5.88. Pyrophosphoric acid, in the amount of 1.13 grams was then added, and stirring continued for another 30 minutes, at which time the final pH was found to be 5.2. The temperature of the mixture was maintained at 40° C. during the foregoing additions, through the use of external cooling.

The resulting dicalcium phosphate dihydrate product was recovered from the slurry by filtration, after which it was dried and milled.

A portion of the dicalcium phosphate dihydrate was then blended with 2% trimagnesium phosphate, by weight of dicalcium phosphate dihydrate, and used to prepare a standard toothpaste formulation which also included sodium monofluorophosphate in an amount equivalent to 1000 ppm. fluoride ion.

The toothpaste formulation was then aged for three weeks at 49° C., after which the amount of water soluble monofluorophosphate remaining was determined. The results are shown in Table I.

EXAMPLE II

A quantity of dicalcium phosphate dihydrate was prepared as in Example 1, except that the slaked lime slurry addition was terminated at a pH of 3.4 ("Terminal pH"). A small amount of pyrophosphoric acid was added and the slurry stirred for an additional 30 minutes, after which the final pH was found to be 3.3. The dicalcium phosphate dihydrate was then used to prepare a standard toothpaste formulation, which was aged and tested for monofluorophosphate compatibility as in Example 1. The results are shown in Table I.

EXAMPLE 3

A slaked lime slurry was prepared by mixing 310 grams CaO with 2400 ml. distilled water at a temperature which varied between 50° C. and 78° C. The slurry was then passed through a 140 mesh sieve and then cooled to room temperature. The slurry was found to contain 124 grams CaO/liter.

A monocalcium phosphate solution was prepared by mixing 358 grams of the slaked lime slurry with 401 grams of 85% $H_3PO_4$ and 608 ml. distilled water.

To the monocalcium phosphate slurry was then added additional slaked lime slurry, at a temperature of 40° C., until the pH of the mixture reached 5.8 (the "Terminal pH was therefore 5.8).

Pyrophosphoric acid, in the amount of 2.0 grams, was then added and the mixture stirred for another 30 minutes. The final pH was then found to be 5.4. The dicalcium phosphate dihydrate product was then recovered by filtration, dried, milled and blended with trimagnesium phosphate as in Example I. A portion of the product was then used to prepare a standard toothpaste formulation, as in the previous examples, and aged for three weeks at 49° C. after which the amount of water soluble monofluorophosphate remaining was determined. The results are shown in Table II.

EXAMPLE 4

The procedure of Example 3 was repeated, except that the addition of lime slurry was terminated at a pH of 5.0 and the final pH after addition of pyrophosphoric acid was 4.7. The monofluorophosphate compatibility test results are shown in Table II.

EXAMPLE 5

The procedure of Example 4 was repeated, except that the terminal pH was 4.5 and the final pH was 4.5. The monofluorophosphate compatibility test results are shown in Table II.

TABLE I

MONOFLUOROPHOSPHATE COMPATIBILITY OF DICALCIUM PHOSPHATE DIHYDRATE
(Product Made Using Recycled Mother Liquor)

| Example | pH | | Compatibility[1] | |
|---|---|---|---|---|
| No. | Terminal | Final | Product | Control[2] |
| 1 | 5.9 | 5.2 | 630 | 650 |
| 2 | 3.4 | 3.3 | 700 | " |

TABLE II

MONOFLUOROPHOSPHATE COMPATIBILITY OF DICALCIUM PHOSPHATE DYHYDRATE
(Product Made Using Distilled Water)

| Example | pH | | Compatibility[1] | |
|---|---|---|---|---|
| No. | Terminal | Final | Product | Control[2] |
| 3 | 5.8 | 5.4 | 640 | 625 |
| 4 | 5.0 | 4.7 | 690 | " |
| 5 | 4.5 | 4.5 | 670 | " |

[1] Monofluorophosphate compatibility, expressed as ppm F-.
[2] The control samples for both tables I and II were taken from the same source.

We claim:

1. A process for preparing dicalcium phosphate dihydrate having improved monofluorophosphate compatibility comprising the steps of:
   (a) reacting a slaked lime slurry with phosphoric acid to form a monocalcium phosphate solution;
   (b) adding to said solution additional slaked lime slurry and pyrophosphoric acid in amounts sufficient to form a dicalcium phosphate dihydrate slurry having a pH ranging from above about 2.2 to below 4.7; and
   (c) separating said dicalcium phosphate dihydrate from said slurry.

2. The process of claim 1 wherein the amount of pyrophosphoric acid added ranges from about 0.1% to about 1.0% by weight of dicalcium phosphate dihydrate to be produced.

3. The process of claim 1 wherein said pH ranges from above about 3.3 up to below 4.7.

4. The process of claim 1 wherein said pH ranges from above about 2.2 up to about 3.3.

* * * * *